United States Patent [19]

Kraus

[11] Patent Number: 5,726,028
[45] Date of Patent: Mar. 10, 1998

[54] METHOD FOR DETECTING DISTURBANCES OF THE PROTEIN C/PROTEIN S SYSTEM

[75] Inventor: Michael Kraus, Marburg, Germany

[73] Assignee: Behring Diagnostics GmbH, Marburg, Germany

[21] Appl. No.: 511,248

[22] Filed: Aug. 4, 1995

[30] Foreign Application Priority Data

Aug. 8, 1994 [DE] Germany .......................... 44 27 785.7

[51] Int. Cl.$^6$ .................................................. C12Q 1/56
[52] U.S. Cl. .............. 435/13; 435/69.2; 435/69.6; 436/69; 530/380; 530/381; 530/382; 530/383; 530/384; 530/385; 514/834
[58] Field of Search .............. 435/13, 69.2, 69.6; 436/69, 86; 530/380, 381, 382, 383, 384, 385

[56] References Cited

U.S. PATENT DOCUMENTS 5,308,756  5/1994  Van De Waart et al. ................ 435/13

FOREIGN PATENT DOCUMENTS

| 0236 985 A2 | 9/1987 | European Pat. Off. . |
| 0406 971 A1 | 1/1991 | European Pat. Off. . |
| WO 91/01382 | 2/1991 | WIPO . |
| WO 93/10262 | 5/1993 | WIPO . |

OTHER PUBLICATIONS

Duchemin et al. (1994) Thromb. Hemostas. 71(3):331–8.
Becker et al. (1985) Thromb. Res. 40: 721–30.
Esmon, C.T., "Protein S and Protein C Biochemistry, Physiology, and Clinical Manifestation of Deficiencies," TCM 2 (6) :214–19 (1992).
Rick et al., "Factor IXa and von Willebrand Factor Modify the Inactivation of Factor VIII by Activated Protein C," J. Lab. Clin. Med. 115(4):415–21 (1990).
Amer et al., "Impairment of the Protein C Anticoagulant Pathway in a Patient with Systemic Lupus Erythematosus, Anticardiolipin Antibodies and Thrombosis," Thromb. Res. 57(2):247–58 (1990).
Bertina et al., "Mutation in Blood Coagulation Factor V Associated with Resistance to Activated Protein C," Nature 369:64–67 (1994).
Bertina, R.M., "Specificity of Protein C and Protein S Assays," Res. Clin. Lab. 20:127–38 (1990).
Duchemin et al., "A New Assay Based on Thrombin Generation Inhibition to Detect Both Protein C and Protein S Deficiencies in Plasma," Thromb. Haemost. 71(3):331–38 (1994).
European Search Report, dated Nov. 9, 1995.

*Primary Examiner*—Robert A. Wax
*Assistant Examiner*—Tekchand Saidha
*Attorney, Agent, or Firm*—Finnegan, Henderson, Farabow, Garrett & Dunner, L.L.P.

[57] ABSTRACT

The present invention relates to a method for detecting disturbances of the protein C/protein S system.

39 Claims, No Drawings

METHOD FOR DETECTING DISTURBANCES OF THE PROTEIN C/PROTEIN S SYSTEM

The present invention relates to a method for detecting disturbances of the protein C/protein S system.

The protein C/protein S system is an important anticoagulant mechanism. In the normal case there is a balanced relation between the coagulant and anticoagulant mechanisms of clotting.

Activation of clotting leads to the conversion of the proenzyme prothrombin into the active protease thrombin. Thrombin itself increases the rate of its production by activating the cofactors factor V and factor VIII proteolytic cleavage. These activated cofactors form, with the proteases factor Xa and IXa active enzyme/cofactor complexes on phospholipid surfaces, the activity thereof being a factor of about 1000 higher than that of the proteases alone. This positive feedback results in almost explosive production of large amounts of thrombin. Thrombin converts fibrinogen into fibrin which, in the normal case, leads to wound closure and wound healing. In order to prevent life-threatening spreading of the clotting, which would lead to blockage of the vascular system in the body, that is to say to thromboses, it is necessary to inhibit both the active protease and the resupply of protease. Active proteases are neutralized in the body by protease inhibitors by the formation of covalent complexes. The stoppage of replenishment initiated by thrombin itself. For this purpose, thrombin binds to the membrane protein thrombomodulin and converts the proenzyme protein C (PC) into the active protease protein Ca (APC). APC in turn forms, with the cofactor protein S (PS), a complex which proteolytically cleaves, and thus inactivates, the active cofactors factor VIIIa and Va. APC-thus stops the strong stimulation by these cofactors.

The importance of the protein C/protein S system is confirmed by the fact that people with inherited or acquired deficiencies or defects in protein C and/or protein S have a higher probability of suffering thromboses, especially recurrent venous thromboses (Esmon, C. T., TCM 2: 214–219, 1992). Besides protein C and protein S, the activity of the system can be influenced by other factors, for example yon Willebrand factor and factor IXa (Rick, M. E., et al., J. Lab. Clin. Med. 115: 415–421, 1990), which are able to protect factor VIIIa from proteolytic breakdown. Acquired disturbances may also derive from the production of lupus anticoagulants. These are antibodies which are directed against phospholipids and which interfere with the binding, which is necessary for the function, of the protease/cofactor complexes to phospholipid surfaces (Amer, L., et al., Thomb. Res. 57: 247–258, 1990). Finally, there has recently been a description of a mutation of factor V which can now be inactivated by APC only very poorly if at all (Bertina, R. M. et al., Nature 369: 64–67, 1994).

Because of the many possible disturbances of the protein C/protein S system which is important for its antithrombotic effect, it is worthwhile in clinical diagnosis to use a screening test which generally indicates a disturbance of this system. This is particularly true when certain disturbances, such as in this case by yon Willebrand factor, factor IXa, lupus anticoagulant or the factor V mutation, can be analyzed only at great expense in laboratories with specific experience thereof. In addition, a screening test which utilizes the principle of the effect of the protein C/protein S system is also able to indicate disturbances whose causes are as yet unknown.

To date, protein C or protein S have been investigated for their functionality as individual factors. For this purpose, the sample or the protein C isolated from the sample is initially added to an excess of a protein C-deficient plasma. The protein C is subsequently activated either by adding thrombin or thrombin and thrombomodulin or by adding a snake venom from *Agkistrodon contortfix*, which is known under the proprietary name Protac® (Pentapharm, Basle, Switzerland). The protein C present in the sample is detected either on the basis of the prolongation of the clotting time owing to the anticoagulant effect of the protein C present in the sample or by conversion of a substrate specific for thrombin. Alternatively, direct chromogenic determination of the protein C activity is also possible after activation with thrombin or Protac® by using a specific substrate for APC.

The protein S determinations take place by mixing the sample with PS-deficient plasma. The stimulating effect of protein S on the anticoagulant activity of APC is measured by determining the prolongation of the clotting time. Either the APC required for this is added, or the protein C in the PS-deficient plasma is activated using Protac®. (A review is given in Bertina, R. M., Res. Clin. Lab. 20: 127–138, 1990).

The methods described to date are suitable only for detecting disturbances of protein C or protein S by the single factor investigated in each case. They are therefore unsuitable as screening tests.

In another method (Amer, L., et al., Thomb. Res. 57: 247–258, 1990) there is modification of the activated partial thromboplastin time (APTT). The APTT is a standard method for detecting clotting disturbances, i.e. it is used to detect tendencies to bleeding. After activation of the sample plasma using an activating surface, in the method of Amer et al. the clotting is started by simultaneous addition of calcium ions and APC. The clotting times are prolonged owing to the anticoagulant effect of the exogenously added APC. This test thus immediately detects certain disturbances of the protein C/protein S system. Since there is exogenous addition of APC, however, it is not possible to detect defects or deficiencies in the protein C in the sample.

Based on the prothrombin time, which is another standard method in coagulation diagnosis, Duchemin, J. et al., (Thromb. Haemost. 71, 331–338, 1994) activate clotting in a sample By adding thromboplastin and calcium. The resulting thrombin activates, on simultaneous addition of thrombomodulin, the protein C in the sample (endogenously). Depending on the functioning of the protein C/protein S system, APC counteracts the production of thrombin. After 15 minutes, further clotting activity is stopped by complexing the calcium ions, and the resulting thrombin is determined by conversion of a specific chromogenic substrate. The amount of thrombin produced is indirectly dependent on the functioning of the protein C protein S system. All disturbances of the protein C/protein S system. In the sample can be detected because the endogenous, protein C is activated. However, there is a particular disadvantage in, the long total measurement time of 16 minutes. Such a time-consuming test is disadvantageous for routine use as screening test. Furthermore, two membrane proteins are required, thromboplastin and thrombomodulin, whose preparation is elaborate and whose stability is limited, especially in the case of thrombomodulin. Finally, a clot is produced in the sample even in the first step, so that this method is possible only in combination with chromogenic measurement methods which measure the conversion by the produced thrombin despite the presence of the clot. Hence, the traditional measurement method which measures the production of the fibrin clot is impossible.

The present invention was therefore based on the technical problem of providing a method which is suitable for complete measurement of the functionality of the protein C/protein S system and can be quantified both with the traditional measurement technique—measurement of the production of a fibrin clot—and with the aid of chromogenic substrates.

The solution to this technical problem comprises the provision of the embodiments disclosed in the patent claims.

It has been found, surprisingly, that disturbances of the protein C/protein S system can be detected in a functional clotting test when endogenous protein C in the sample is activated by adding a protein C activator to the sample, which leads in the normal case to prolongation of the clotting time, presumably because of the breakdown of the activated cofactors factor Va and factor VIIIa. Less pronounced prolongation of the clotting time indicates disturbances of this natural anticoagulative system, for which reason this test is also suitable in particular as screening test.

In the method according to the invention, the endogenous protein C in the sample is utilized for checking the functionality of the protein C/protein S system. The test is based on a modification of the APTT. A protein C activator, contact phase activator, phospholipids and the sample are first mixed in a test vessel and then incubated. In this phase there is, as customary in the APTT, activation of the proteases factor XII, prekallikrein and factor XI. In addition, the endogenous protein C in the sample is activated by the protein C activator and forms with the protein S in the sample active APC/protein S complexes on phospholipid surfaces. After the incubation, the clotting is induced by adding calcium ions, and the resulting APC/protein S complexes delay clot formation as already described above.

The method according to the invention differs from Duchemin et al. In that protein C is activated not by the thrombin in the sample but by adding a protein C activator. This allows the measurement time to be considerably reduced. Thus, as detailed in Example 1, even short incubation times of 2 minutes are completely sufficient to be able to obtain information about the functioning of the protein C/protein s system. Finally, the detection takes place by determination of the clotting time, so that it is possible to use apparatus measuring either by the traditional method (determination of the onset of clot formation) or by a chromogenic method (conversion of a chromogenic substrate).

In contrast to earlier methods for protein C or protein S determination, the sample is not mixed with a corresponding deficient plasma so that only the factors in the sample itself are included in the determination. Finally, Example 2 shows that in the method of Amer et al. (1990) on addition of exogenous APC a protein C deficiency is not detected, whereas this is the case in Example 1 using the method according to the invention.

From the viewpoint of hemostasiology, the body is exposed to two dangers through which the blood may be deprived of its function as organ: on the one hand blood loss, and on the other hand intravascular clotting. There are accordingly diagnostic methods available for detecting tendencies to bleeding and methods for detecting tendencies to clotting. The method according to the invention—for detecting disturbances of the protein C/protein S system belongs to the class of detection methods for detecting a tendency to clotting. However, the process according to the invention is surprisingly based on a modification of a standard method for detecting tendencies to bleeding, the activated partial thromboplastin time (APTT). Surface activators of the contact phase of the clotting system which can be used are all materials according to the state of the art, such as, for example, kaolin, silica, glass or ellagic acid.

The protein C in the sample is activated by proteolysis with a suitable enzyme. Preferred enzymes are those which do not activate or otherwise influence any other factors in the clotting system apart from protein C. Particularly, preferred therefore are protein C activators from the venom of snakes. Such as, for example, *Agkistrodon contortrix contortrix*, *Agkistrodon bilineatus* or *Agkistroron halys halys*.

The concentration of the protein C activator is moreover chosen so that, in conjunction with the duration of action on protein C activation (incubation time), a suitable prolongation of the clotting time in the plasma is produced in the test. A suitable prolongation of the clotting time compared with the clotting time in the absence of a protein C activator is one which, on the basis of the type of apparatus used, allows significant differences from normal plasmas to be detected. The prolongation is preferably at least 30%, particularly preferably at least 100%, very particularly preferably at least 200%.

It is also conceivable to activate the protein C in the sample completely by previous incubation with a protein C activator. In this case, however, it is necessary to dilute the sample appropriately, or only small amounts of sample can be used, so that the sample remains clottable.

If the protein C activator used does not require phospholipids for activation of protein C, it is also possible for the incubation of surface activator, sample and protein C activator to take place in the absence of phospholipids, and for the latter to be added only later. The sequence of addition of surface activator, sample, protein C activator and, where appropriate, phospholipids can be varied. A reagent which contains an activating surface, phospholipids and a protein C activator therefore preferred (see Example 3). Particularly preferred as further additive in a reagent is a chromogenic substrate for thrombin so that chromogenic determination of the clotting time is also possible (see Example 4).

Combination with additional reagents which permit more detailed specification of the defect found is also possible. Thus, in the case of suspected protein C deficiency or defect, the sample can be mixed with a solution containing protein C. If a protein C deficiency or defect was actually the cause of an abnormally short clotting time in the method according to the invention, it is neutralized by the addition (see Example 5). Correspondingly, it is possible to add protein S when there is suspicion of protein s deficiency or defect, factor V (F.V) or a solution enriched with factor V when there is suspicion of abnormal factor V or phospholipids to neutralize inhibitory antibodies ("Lupus anticoagulant"). These additions are preferably added in an amount such that the test mixture contains in each case the functional amount of the particular additional component which would also result with a normal plasma. It is sensible go make these additions before adding the protein C activator. Previous incubation of the additions with the sample is preferred. A preincubation of this type is particularly preferred when phospholipids are added to neutralize inhibitory antibodies.

Since the method is based on a modification of a standard method for identifying a risk of hemorrhage, it is also possible to use other conventional clotting methods besides the APTT, such as the prothrombin time (PT; see Example 6) or the Russell's viper venom time (RVVT; see Example 7). The prothrombin time is based on the use of a reagent which, besides phospholipids and calcium chloride, contains tissue factor (thromboplastin; "tissue factor") which activates the so-called extrinsic pathway of clotting. In the RVVT, snake venom, preferably of the species *Vipera russellii*, is used to activate the clotting factors X and V, which then directly, without further intermediate steps, generate thrombin from prothrombin. The factor VIII-dependent clotting cascade is bypassed in both methods: Variations in concentration of factor VIII have the greatest effect on the result in the APTT because, on the one hand, factor VIII speeds up, as cofactor, the clotting processes by a factor of about 1,000 and, on the other hand, the factor VIII concentrations may commonly vary widely in patients. Thus, by comparison with APTT, use of a PT or RVVT results in a more specific method which depends less on the procoagulant factors than, on the contrary, now only on the factors of the protein C/protein S system (Example 8).

The following examples are intended merely to explain the invention but not in any Way to restrict the claims.

EXAMPLE 1

Determination of the clotting the with activation of endogenous protein C

The clotting time was determined using a Schnitger & Gross mechanical coagulometer (from Amslung). All the reagents were commercial products of Behringwerke AG or usual laboratory chemicals. The following samples were investigated: a pool from normal blood donors (standard human plasma), protein C-deficient plasma, protein S-deficient plasma and a plasma with a genetic defect in factor V so that factor Va produced is only poorly inactivated by APC.

The consents of a container of protein C activator for Berichrom® protein C (contains protein C activator from the venom of *Agkistrodon contortrix contortrix*) was dissolved in 10 ml of physiological saline. Pathromtin®, a phospholipid mixture from human placenta, was dissolved in 5 ml of kaolin suspension as surface activator. The calcium chloride solution (25 mM) and the protein C. activator solution were warmed to +37° C. before use.

100 µl of protein C activator solution

100 µl of Pathromtin®

100 µl of plasma sample were successively pipetted into a measuring tube. Incubation was then carried out at +37° C. for 2 minutes, and e he clotting time was started by adding 100 µl of calcium chloride solution. At the same time, an integral stop-clock was switched on and the time until a clot was detected was measured.

The clotting time of the samples without activation of protein C, i.e. on addition of 100 µl of physiological saline in place of the protein C activator solution, was also determined.

Table 1 summarizes the resulting clotting times (means of duplicate determinations). Clotting times of about 42 sec without and of 145 sec with PC activator were obtained with a pool of citrated plasma from normal blood donors (SHP). This prolongation of about 103 sec achieved due to the activity of the protein C/protein S system was distinctly less in the samples which had a protein C (PC-DP) or protein S deficiency (PS-DP). The plasma with a mutated factor V (F.V D) also showed a distinctly smaller prolongation of the clotting time.

TABLE 1

Clotting times in the absence and presence of a protein C activator to activate the endogenous protein C in various plasmas with defects in the protein C/protein S system.
Data in seconds, SHP = standard human plasma, PC-DP = protein C-deficient plasma, PS-DP = protein S-deficient plasma, F.V D = factor V gene defect.

|  | SHP | PC-DP | PS-DP | F.V D |
|---|---|---|---|---|
| Without APC | 41.6 | 43.2 | 57.1 | 41.6 |
| With APC | 45.0 | 46.6 | 120.3 | 76.7 |
| Prolongation | 103.4 | 3.4 | 63.2 | 35.1 |

EXAMPLE 2

Determination of the clotting time in the presence of exogenous protein C

The clotting time was determined using a Schnitger & Gross mechanical coagulometer (from Amelung). All the reagents were Commercial products of Behringwerke AG or usual laboratory chemicals. The samples corresponded to those in Example 1.

The contents of a container of APC reagent for APC sensitivity reagents (contains human activated protein C and calcium chloride) was dissolved in 5 ml of distilled water. Pathromtin® was used as in Example 1 as surface activator and phospholipid mixture. The APC reagent was warmed to +37° F. before use.

100 µl of Pathromtin®

100 µl of plasma sample were pipetted successively into a measuring tube. Incubation was then carried out at +37° C. for 2 minutes, and the clotting time was started by adding 100 µl of APC reagent. At the same time, an integral stopclock was switched on and the time until a clot was detected was measured.

The clotting time of the samples without activation of protein C, i.e. on addition of 100 µl of calcium chloride solution in place of APC reagent, was also determined.

Table 2 summarizes the resulting clotting times (means of duplicate determinations). The clotting times obtained with a pool of citrated plasma from normal blood donors (SHP) were about 37 sec without and about 170 sec in the presence of added exogenous APC. This prolongation of about 133 sec obtained therewith was distinctly less in the protein S-deficient plasma (PS-DP) but especially in the plasma with a mutated factor V (F.V D). On the other hand, a protein C deficiency was not detected in this method, in contrast to the method according to the invention. On the contrary, because of the slight factor deficiency, evident from the somewhat prolonged APTT (=clotting time without APC), the clotting time in the presence of APC was even clearly prolonged beyond that of SHP. This method is unsuitable, in contrast to the method according to the invention, for detecting all defects in the protein C/protein S system.

TABLE 2

Clotting times in the absence and presence of added exogenous activated protein C in various plasmas with defects in the protein C/protein S system.
Data in seconds, SHP = standard human plasma, PC-DP = protein C-deficient plasma, PS-DP = protein S-deficient plasma, F.V D = factor V gene defect.

|  | SHP | PC-DP | PS-DP | F.V D |
|---|---|---|---|---|
| Without PC activator | 36.8 | 41.9 | 64.9 | 35.7 |
| With PC activator | 169.6 | 298.0 | 108.2 | 54.5 |
| Prolongation | 132.8 | 256.1 | 43.3 | 18.8 |

Table 3 summarizes the clotting times (means of duplicate determinations) obtained with the various plasmas. The clotting times obtained with a pool of citrated plasma from normal blood donors (SHP) were 37.6 sec without and 131.7 sec with PC activator in the APTT reagent. In analogy to the results detailed in Example 1, the prolongations of the clotting time were distinctly less in a protein C- (PC-DP), a protein S-deficient (PS-DP) or in a plasma with a mutated factor V (F.V D). This example also shows that a deficiency of factors which are connected primarily not with the protein C/protein s system but with thrombin generation, for example a factor V or a factor VIII deficiency, leads in the presence of a protein C activator not to a shortening but, on the contrary, to a prolongation of the clotting time. These plasmas can then no longer be clotted, i.e. the measurement was stopped after 300 sec (">300" in Table 3).

TABLE 3

Clotting times in various plasmas on use of an APTT reagent without (Pathromtin ®) and with a protein C activator (monoreagent).
Data in seconds. SHP = standard human plasma, PC-DP = protein C-deficient plasma, PS-DP = protein S-deficient plasma, F.V-DP = factor V-deficient plasma, F.VIII-DP = factor VIII-deficient plasma, F.V D = factor V gene defect.

|  | SHP | PC-DP | PS-DP | F.V D | F.V.-DP | F.VIII-DP |
|---|---|---|---|---|---|---|
| Pathromtin ® | 37.6 | 42.2 | 54.2 | 35.6 | >300 | 88.6 |
| Monoreagent | 131.7 | 42.5 | 79.4 | 47.8 | >300 | >300 |
| Prolongation | 94.1 | 0.3 | 25.2 | 12.2 | — | — |

EXAMPLE 3

Determination of the clotting the with activation of the endogenous protein C using a monoreagent.

The clotting time was determined in a Schnitger & Gross mechanical coagulometer (from Amelung). All the reagents were supplied by Behringwerke AG. In addition to the samples corresponding to Example 1, a factor V-deficient plasma (F.V-DP) and factor VIII-deficient plasma (F.VIII-DP) were also investigated.

The contents of two containers of protein C activator for Berichrom® protein C were each dissolved in 2.5 ml of kaolin suspension. These solutions (5 ml) were in turn used to dissolve the contents of 1 container of Pathromtin®. This monoreagent thus contains phospholipids, kaolin as surface activator and an activator for protein C. The calcium chloride solution (25 mM) and the monoreagent were warmed to +37° C. before use.

100 µl of monoreagent
100 µl of plasma sample
were pipetted successively into a measuring tube incubation was then carried out at +37° C. for 2 minutes, and the clotting time was started by adding 100 µl of calcium chloride solution. At the same time an integral stopclock was switched on and the time until a clot was detected was measured.

The clotting time of the samples without activation of protein C, i.e. on use of commercial Pathromtin®, was also determined.

EXAMPLE 4

Determination of the clotting time with activation of endogenous protein C using a chromogenic substrate for thrombin.

The clotting time was determined in a Behring coagulation timer (BCT; Behringwerke), a photometric coagulometer. All the reagents were supplied by Behringwerke AG. The samples correspond to those from Example 1.

The contents of a container of protein C activator for Berichrom® C was dissolved in 10 ml of physiological saline. Pathromtin® EL was used as APTT activator reagent. This is a suspension of phospholipids from soybeans with silica particles as surface activator. A mixture of calcium chloride solution (25 mM) and 0.2 mM BCP-100, a chromogenic thrombin substrate, was used as starting reagent.

The pipetting was carried out automatically by the apparatus. The starting reagent and the protein C activator solution are warmed to +37° C. by the apparatus immediately before use.

70 µl of Pathromtin® SL
0 µl of protein C activator or only physiological saline
70 µl of sample
were pipetted successively into a measuring cuvette. Incubation was then. Carried out at +37° C. for 2 minutes, and the measurement was started by adding 70 µl of starting reagent. The time until there was an increase of 0.3 in the extinction at 405 nm was recorded.

Table 4 lists the times obtained with the various plasmas. In analogy to the classical clotting method (detection of the formation of a fibrin clot) all the plasmas with a disturbance of the protein C/protein S system are found to be shorter than a normal plasma pool also on use of a chromogenic substrate.

TABLE 4

Chromogenic determination of thrombin production with and without activation of endogenous protein C in plasmas with various disturbances of the protein C/protein S system. Data in seconds until an increase of 0.300 when extinction at 405 nm occurred. SHP = standard human plasma, PC-DP = protein C-deficient plasma, PS-DP = protein S-deficient plasma, F.V D = factor V gene defect.

|  | SHP | PC-DP | PS-DP | F.V D |
|---|---|---|---|---|
| Without PC activator | 73.9 | 95.1 | 95.6 | 73.4 |
| With PC activator | 111.3 | 100.2 | 120.6 | 91.4 |
| Prolongation | 37.4 | 5.1 | 25.0 | 18.0 |

EXAMPLE 5

Identification of a defect in the protein C/protein S system by modification of the screening method.

The clotting time was determined as described in Example 3 and in Example 4 once by measuring the clot formation with a monoreagent and by measuring the thrombin formation in a separate mixture. This screening test is also suitable for differential diagnosis. For this purpose, the mixtures detailed in Example 3 and 4 were modified as follows. As first step, 5 µl of a protein C-containing solution were pipetted. The concentration was chosen so that the resulting protein C concentration was I unit based on the sample volume. Addition of sample and reagents then takes place normally.

It is evident from Table 5 that with various methodological variants of the determination method it is unambiguously possible to differentiate a protein C deficiency from, for example, a protein S deficiency. Whereas addition of protein C to a protein C-deficient plasma compensated the difference in measurements for the mixtures with and without addition of a protein C activator, this was not the case with a protein S-deficient plasma. Thus, this method can also be used for differential diagnosis by, slight modifications.

TABLE 5

Modification of the method according to the invention for differential diagnosis. Samples in which the differences in the clotting times in the absence and presence of a protein C activator differed from normal plasma were mixed with 1 U of protein C per ml of plasma, and the clotting times were determined anew. The determination took place on the one hand by a traditional method using a monoreagent (A), and on the other hand in a multi-stage chromogenic method (B). Data in seconds. SHP = standard human plasma, PC-DP = protein C-deficient plasma, PS-DP = protein S-deficient plasma.

(A) Traditional method

|  | SHP | PC-DP without | + 1 U PC | PS-DP without | + 1 U PC |
|---|---|---|---|---|---|
| Without PC activator | 37.6 | 42.2 | 39.7 | 54.2 | 106.1 |

TABLE 5-continued

Modification of the method according to the invention for differential diagnosis. Samples in which the differences in the clotting times in the absence and presence of a protein C activator differed from normal plasma were mixed with 1 U of protein C per ml of plasma, and the clotting times were determined anew. The determination took place on the one hand by a traditional method using a monoreagent (A), and on the other hand in a multi-stage chromogenic method (B). Data in seconds. SHP = standard human plasma, PC-DP = protein C-deficient plasma, PS-DP = protein S-deficient plasma.

| With PC activator | 131.7 | 42.5 | 143.4 | 79.4 | 117.0 |
|---|---|---|---|---|---|
| Prolongation | 94.1 | 0.3 | 103.7 | 25.2 | 10.9 |

(B) Chromogenic method

| Without PC activator | 73.9 | 85.3 | 93.3 | 95.6 | 96.3 |
|---|---|---|---|---|---|
| With PC activator | 111.3 | 92.3 | 149.0 | 120.6 | 122.3 |
| Prolongation | 37.4 | 7.0 | 55.7 | 25.0 | 26.0 |

EXAMPLE 6

Determination of the clotting time with activation of endogenous protein C using the prothrombin time.

The clotting time was determined in a Schnitger & Gross mechanical coagulometer (from Amelung). All the reagents were supplied by Behringwerke AG.

Thromborel S®, a tissue factor/phospholipid preparation from human placenta, was diluted 1:1,000 in 50 mM Tris buffer, pH 7.4, 0.01% Phospholipon 25. 5 ml of this solution were used to dissolve the contents of one container of protein C activator for Berichrom protein C as described in Example 3. This solution was warmed to 37° C. before use and was used in place of the APTT-based monoreagent as described in Example 3.

Furthermore, the clotting time of the samples without activation of protein C, i.e. on use of commercial Pathromtin®, was determined.

Table 6 summarizes the clotting times (means of duplicate determinations) obtained with the various plasmas. In analogy to the results detailed in Example 1, the prolongations of the clotting time were distinctly less in a protein C-(PC-DP), a protein S-deficient (PS-DP) or in a plasma with a mutated factor V (F.V D).

TABLE 6

Clotting times in various plasmas on use of a PT reagent (Thromborel S ®) with a protein C activator (monoreagent). Data in seconds. SHP = standard human plasma, PC-DP = protein C-deficient plasma, PS-DP = protein S-deficient plasma, F.V D = factor V gene defect.

| SHP | PC-DP | PS-DP | F.V D |
|---|---|---|---|
| 103.6 | 49.6 | 54.5 | 69.6 |

EXAMPLE 7

Determination of the clotting time with activation of endogenous protein C using the RVVT.

The clotting time was determined in a Behring coagulation timer (BCT; Behringwerke), a photometric coagulometer. LA-Confirm supplied by Gradipore ETD (North Ryde, NSW, Australia) was used as RVVT reagent. All the other reagents were supplied by Behringwerke AG. The samples correspond to those from Example 1.

The contents of a container of protein C activator for Berichrom® protein C were dissolved in 10 ml of physiological saline. The RVVT reagent was dissolved as instructed. All the reagents were brought to +37° C. before use by the apparatus.

50 µl of sample

50 µl of protein C activator or only physiological saline were pipetted successively into a measuring cuvette. Incubation was then carried out at +37° C. for 2 minutes, and the measurement was started by adding 100 µl of RVVT reagent. The time until there was an increase of 0.3 in the extinction and 405 nm was recorded.

Table 7 lists the times obtained with the various plasmas. In analogy to the other classical clotting methods (APTT, PT), all the plasmas with a disturbance of the protein C/protein S system are found to be shorter than a normal plasma pool also on use of an RVVT reagent.

TABLE 7

Clotting times in various plasmas on use of an RVVT reagent after incubation of the sample in the presence or without addition of a protein C activator.
Data in seconds. SHP = standard human plasma, PC-DP = protein C-deficient plasma, PS-DP = protein S-deficient plasma, F.V D = factor V gene defect.

|  | SHP | PC-DP | PS-DP | F.V D |
| --- | --- | --- | --- | --- |
| without PC activator | 43.6 | 44.8 | 49.4 | 43.4 |
| with PC activator | 125.6 | 49.1 | 74.1 | 61.3 |

EXAMPLE 8

Dependence of the determination of factor VIII using the APTT or the PT with activation of endogenous protein C A standard human plasma was mixed with a factor VIII-deficient plasma, or Beriate®, a factor VIII concentrate (Behringwerke AG), was added, in order to simulate the effect of factor VIII on the determination of the clotting time after activation of endogenous protein C. Determination using an APTT took place as described in Example 1, and determination by means of PT took place as described in Example 6.

Table 8 lists the clotting times obtained on the basis of an APTT or PT. It is evident that the unwanted interference of factor VIII on evaluation of the functionality of the protein C system is clear in the case of the APTT while it virtually did not occur in the PT-based method.

TABLE 8

Clotting times as a function of the factor VIII concentration on use of an APTT or of a PT reagent after incubation of the sample with a protein C activator. (Data in sec.)

| Factor VIII (U/ml) | APTT | PT |
| --- | --- | --- |
| 0.25 | 206 | 114 |
| 0.5 | 147 | 111 |
| 1.0 | 96 | 104 |

TABLE 8-continued

Clotting times as a function of the factor VIII concentration on use of an APTT or of a PT reagent after incubation of the sample with a protein C activator. (Data in sec.)

| Factor VIII (U/ml) | APTT | PT |
| --- | --- | --- |
| 1.5 | 79 | 102 |
| 2.0 | 65 | 109 |
| 3.0 | 60 | 107 |
| 4.0 | 54 | 107 |

I claim:

1. A method for the qualitative detection and quantitative determination of the functional activity of the protein C/protein S system of clotting in a sample of a plasma, comprising the steps of:
   (a) adding an activator of protein C to the diluted or undiluted sample, wherein the sample is not mixed with a second plasma deficient in PC or PS;
   (b) optionally adding a contact phase activator;
   (c) incubating the reaction mixture;
   (d) starting the clotting process by adding calcium ions or other agents that induce clotting, or both; and
   (e) determining the clotting activity.

2. The method as claimed in, claim 1, wherein the protein C activator is selected from the group of protein C activators which predominantly or exclusively activate protein C.

3. The method as claimed in claim 1, wherein the reagents for activating clotting factors, or the clotting methods for detecting tendencies to bleeding comprise determination of the activated partial thromboplastin time (APTT), of the prothrombin time (PT) or of the Russell's viper venom time (RVVT).

4. The method as claimed in claim 1, wherein a contact phase activator is selected from the group consisting of kaolin, silica, glass and ellagic acid.

5. The method as claimed in claim 1, wherein the concentration of the protein C activator is adjusted so that the clotting time for a normal plasma is prolonged by at least 30%.

6. The method as claimed in claim 1, wherein the incubation time in step c) is adjusted so that the clotting time for a normal plasma is prolonged by at least 30%.

7. The method as claimed in claim 1, wherein another incubation takes place between step a) and b).

8. The method as claimed in claim 1, wherein
   i) the addition of an activator of protein C,
   ii) the addition of a contact phase activator and
   iii) the start of the clotting process by adding calcium ions
takes place simultaneously or successively at .short time intervals.

9. The method as claimed in claim 1, wherein a chromogenic substrate for determining the clotting activity is used in step e).

10. The method as claimed in claim 1, wherein phospholipids are added to the mixture before step c).

11. The method as claimed in claim 1, wherein phospholipids are added to the mixture after step c).

12. The method as claimed in claim 10, wherein phospholipids are selected from the group of phospholipids which bring about the attachment of enzyme/cofactor complexes to the resulting surfaces.

13. The method as claimed in claim 1, wherein the time until a clot detectable by mechanical, mechano-optical or turbidimetric measurement methods is produced is used to determine the clotting activity in step e).

14. The method as claimed in claim 10, wherein the conversion of a chromogenic substrate for thrombin is used for the photometric determination of the clotting activity in step e).

15. A composition for use in a method as claimed in claim 1, wherein the reagent contains the protein C activator, the contact phase activator and phospholipids in a formulation customary for in vitro diagnosis.

16. The method as claimed in claim 1, wherein further components which are suitable for compensating for endogenous deficits in the protein C/protein S system are added in one of steps a) to e).

17. The method as claimed in claim 16, wherein further components are selected from the group: protein C, protein S, factor V or phospholipids.

18. The method as claimed in claim 17, wherein the proteins employed are preferably of human origin.

19. The method as claimed in claim 17, wherein the proteins employed, are preferably of animal origin.

20. The method as claimed in claim 16, wherein the concentration of the further components is selected so that, in a suitable mixture with the sample, they compensate for a disturbance in the protein C/protein S system based on a deficiency or defect in these further components.

21. The method as claimed in claim 20, wherein the concentration of the further components is selected so that after mixing the sample contains that functional amount of substance which is to be found in a nodal plasma.

22. The method as claimed in claim 20, wherein the further component is factor V, and the concentration of factor V is chosen so that after mixing the sample contains an at least two-fold excess over the amount of functional factor V which is to be found in a normal plasma.

23. The method as claimed in claim 16, wherein the mixing of the sample with the further component(s) takes place before adding the protein C activator.

24. The method as claimed in claim 1, wherein no contact phase activator is used, and the clotting based on the prothrombin time can be induced with reagents which contain tissue factor and phospholipids.

25. The method as claimed in claim 24, wherein the tissue factor can be of natural or recombinant origin.

26. The method as claimed in claim 24, wherein the tissue factor-containing reagent already contains a protein C activator, or the addition of the tissue factor takes place separate from the addition of the protein C activator.

27. The method as claimed in claim 1, wherein no contact phase activator is used, and the clotting based on the RVVT is carried out with reagents which contain the factor X and factor V activating factors from snake venom and phospholipids.

28. The method as claimed in claim 27, wherein the factor X and factor V activating factors are purified or are added by adding unfractionated snake venom to the reagent.

29. The method as claimed in claim 27, wherein the reagent containing factor X and factor V activating factors already contains a protein C activator, or the addition of the factor X and factor V activating factors takes place separate from the addition of the protein C activator.

30. The method as claimed in claim 1, wherein the protein C activator is selected from the group consisting of snake venom enzymes.

31. The method as claimed in claim 30, wherein the protein C activator is the venom from the Agkistrodon genus.

32. The method as claimed in claim 1, wherein at least the incubation in step c) takes place at 36°–38° C.

33. The method as claimed in claim 1, wherein the concentration of the protein C activator is adjusted so that the clotting time for a normal plasma is prolonged by at least 100%.

34. The method as claimed in claim 1, wherein the concentration of the protein C activator is adjusted so that the clotting time for a normal plasma is prolonged by at least 200%.

35. The method as claimed in claim 1, wherein the incubation time in step c) is adjusted so that the clotting time for a normal plasma is prolonged by at least 100%.

36. The method as claimed in claim 1, wherein the incubation time in step c) is adjusted so that the clotting time for a normal plasma is prolonged by at least 200%.

37. The method as claimed in claim 11, wherein phospholipids are selected from the group consisting of phospholipids which bring about the attachment of enzyme/cofactor complexes to the resulting surfaces.

38. The method as claimed in claim 16, wherein the further component or components, incubated for a time of 1–10 minutes, and protein C; activator is subsequently added.

39. A test kit for use in a method as claimed in claim 1 which contains a reagent comprising a protein C activator, a contact phase activator, and phospholipids in a formulation for in vitro diagnosis.

* * * * *

UNITED STATES PATENT AND TRADEMARK OFFICE
CERTIFICATE OF CORRECTION

PATENT NO. : 5,726,028
DATED : March 10, 1998
INVENTOR(S) : Michael KRAUS

It is certified that error appears in the above-identified patent and that said Letters Patent is hereby corrected as shown below:

Claim 2, column 12, line 28, after "claimed in", delete ",".

Claim 3, column 12, line 35, after "(PT)", insert --,--.

Claim 8, column 12, line 53, ".short" should read --short--.

Claim 15, column 13, line 7, "far" should read --for--.

Claim 19, column 13, line 21, after "employed", delete ",".

Claim 21, column 13, line 30, "nodal" should read --normal--.

Claim 38, column 14, line 39, after "wherein the", insert --sample is mixed with a--.

UNITED STATES PATENT AND TRADEMARK OFFICE
CERTIFICATE OF CORRECTION

PATENT NO. : 5,726,028
DATED      : March 10, 1998
INVENTOR(S): Michael KRAUS

It is certified that error appears in the above-identified patent and that said Letters Patent is hereby corrected as shown below:

Claim 38, column 14, line 41, after "protein C", delete ";".

Signed and Sealed this

Eighth Day of December, 1998

Attest:

BRUCE LEHMAN

*Attesting Officer*            *Commissioner of Patents and Trademarks*